US00PP10732P

United States Patent [19]

Wilkins

[11] Patent Number: Plant 10,732

[45] Date of Patent: Dec. 22, 1998

[54] ELM NAMED 'PRINCE RICHARD'

[76] Inventor: Curtis W. Wilkins, P.O. Box 143, Glen Flora, Tex. 77443

[21] Appl. No.: 769,414

[22] Filed: Dec. 19, 1996

[51] Int. Cl.[6] ..... A01H 5/00

[52] U.S. Cl. ..... Plt./53.3

[58] Field of Search ..... Plt./53.3

*Primary Examiner*—Elizabeth C. Kemmerer

*Attorney, Agent, or Firm*—Arnold, White & Durkee

[57] ABSTRACT

A new elm is described which is characterized by its high density branching and dwarf to semi-dwarf size. The new tree is superior in durability and resistance to temperature extremes in comparison to other varieties of *Ulmus parvifolia* and has similar resistance to insects and disease. Tree size is approximately 60% of other standard varieties and the deep green densely borne foliage on numerous branches gives it a rich, full and rounded apearance that makes it attractive to the consumer and enhances commercial value.

2 Drawing Sheets

BACKGROUND OF THE NEW PLANT

The present invention relates to a new and distinct variety of a Chinese elm, *Ulmus parvifolia,* which originated as a chance seedling in a cultivated area. The parents of the new elm variety are unknown. Several distinct and unusual characteristics distinguish the new plant from presently well known varieties such *Ulmus parvifolia, Ulmus parvifolia* 'Drake', *Ulmus parvifolia,* ('Emer I' U.S. Plant Pat. No. 7,551, and *Ulmus parvifolia,* ('Emer II' U.S. Plant Pat. No. 7,552). The inventor observed the tree growing uncharacteristically in a nursery environment in Texas on his nursery ground planted by him in a one gallon container and took particular note of the distinctions between it and other well known elms.

Asexual reproduction of the new variety in Texas by softwood stem cuttings placed under a greenhouse intermittent mist has shown that the new characteristics are permanently fixed through successive propagations.

'Prince Richard' is an attractive, small, rounded head, dwarf to semi-dwarf tree, which is prominently distinguished by its overall size, high density branching, rounded head, and smaller leaves with shorter internode length. The new plant has endured the same growing conditions in southeast Texas during 1989 to 1996 as standard varieties of *Ulmus parvifolia*. It exhibits superior foliage resistance to summer heat and has comparable resistance to cold as other standard elms. It appears to be no more susceptible to insects and disease than any other variety of *U. parvifolia*. 'Prince Richard' has been established as moderately easy to asexually propagate by means of stem cuttings which root with about 95% take. The dwarf size and bud and foliage traits of the clone appeared to be identical to the parent, 'Prince Richard'.

The following characteristics distinguish the new elm from other *Ulmus parviofolia* commercially known and used in the nursery industry.

The following table summarizes some of the differences between 'Prince Richard', Chinese, and 'Drake' Elms. Measurements were taken at the end of the growing season on mature leaves.

TABLE 1

| | 'Prince Richard' | Chinese | 'Drake' |
|---|---|---|---|
| Height at 5 years | 2.1 m | 3.9 m | 3.8 m |
| Spread | 1.5 m | 1.8 m | 1.8 m |

TABLE 1-continued

| | 'Prince Richard' | Chinese | 'Drake' |
|---|---|---|---|
| Trunk caliper @ 6" | 4.4 cm | 5.0 cm | 5.7 cm |
| Leaf size (cm × cm) | 3.0 × 1.8 | 5.8 × 2.9 | 4.2 × 2.2 |
| # Lateral branches per meter of trunk | 48 | 15 | 20 |
| Crotch angle | 30–40° | 40–50° | 50–60° |
| Internode length | 0.5 cm | 2.4 cm | 2.0 cm |
| Leaf color | RHS139A | RHS136B | RHS139A |

DESCRIPTION OF THE DRAWINGS

Photograph 1 shows a comparison of the branches of 'Prince Richard' on the left and a Chinese elm, *U. parvifolia* on the right depicting the smaller, darker green leaves, denser branching, and the shorter internode length of 'Prince Richard'.

Photograph 2 depicts a full side view of a 5 year old 'Prince Richard' specimen tree currently in production in a 24" redwood box.

DESCRIPTION OF THE NEW TREE

Branching and growth habits: The deciduous variety has high branching density caused by the shorter internode length and the extra branchlets that tend to occur on the many fine branches. The tree appears to be dwarf to semi-dwarf in size when compared to standard *U. parvifolia* in current production. Moreover, the branching produces an extremely global to rounded head when compared to known varieties of *U. parvifolia.* The following measurements of mature growth were taken from a group of 5 year old container grown trees at the end of the growing season.

Height: The new tree is 2.1 m in height, 1.5 m in spread with a single trunk characteristic of 4.4 cm in caliper.

Vigor and Style: The tree does not form a center leader but rather forms a rather global to rounded head. New growth is only 25–31 cm per growing season in Southeast Texas.

Main branches: Main branches generally are 100 cm in length, secondary branches are 35 to 48 cm in length, and the branchlets being 10 to 15 cm in length at maturity. Branching is alternate with typical branch angles ranging from 30 to 40 degrees.

Internode length: A distinguishing characteristic, the internode length, is 0.5 cm to 1.0 cm.

Resistance to insects and disease: This tree has shown no more resistance or susceptibility to diseases and insects that normally infest *U. parvifolia* cultivars. The two have been grown side by side and received the same preventative sprays for the last 5 years in a nursery environment.

Leaves: Alternate, simple, serrate to crenate leaf margin. 3.0 cm long, 1.8 cm wide, oval to acute apex, oblique base, lustrous dark green above (The R.H.S. 139A), medium gray green beneath (The R.H.S.191A), pinnate venation, glabrous above and beneath, petiole 0.2 cm in length, light green (The Royal Horticultural Society 145B) and glabrous.

Fall Coloration: During autumn, the leaves are retained by the tree through a series of frosts until about December 15th in Southeast Texas. The leaves exhibit no fall color other than yellow (The R.H.S. 12A).

Stem and trunk: Smooth, fine textured, medium gray brown with small organish lenticels, glabrous. At 5 years of age this new cultivar has not exhibited any exfoliating characteristics of the bark.

Fruit: To date this cultivar has not exhibited any flowers or fruit, probably due to the constant active vegetative growth in a nursery environment.

Propagation: Softwood cuttings have been taken from the parent seedling and subsequent generations for the past 7 years. Cuttings were stripped of basal foliage, dipped in 0.8 kiba solution, placed in a 100% pine bark medium under intermittent mist 90–95% rooting has been consistent from year to year.

What is claimed is:

1. A new and distinct variety of *Ulmus parvifolia* plant as herein described and illustrated, primarily distinguished by its overall height, rounded head, and high density branching.

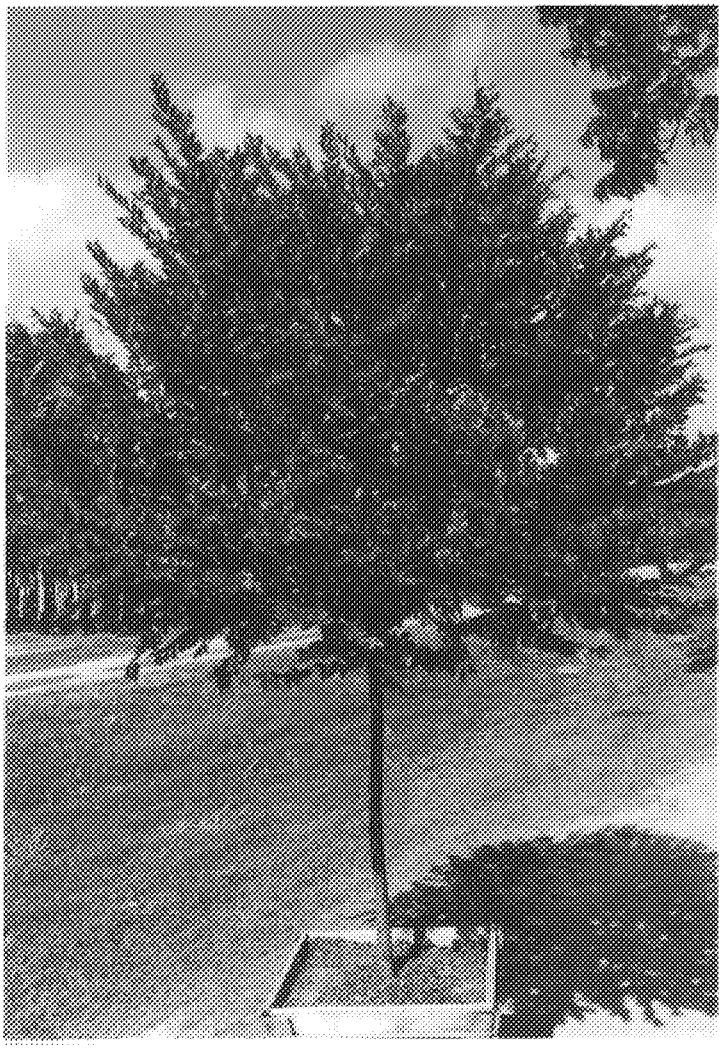

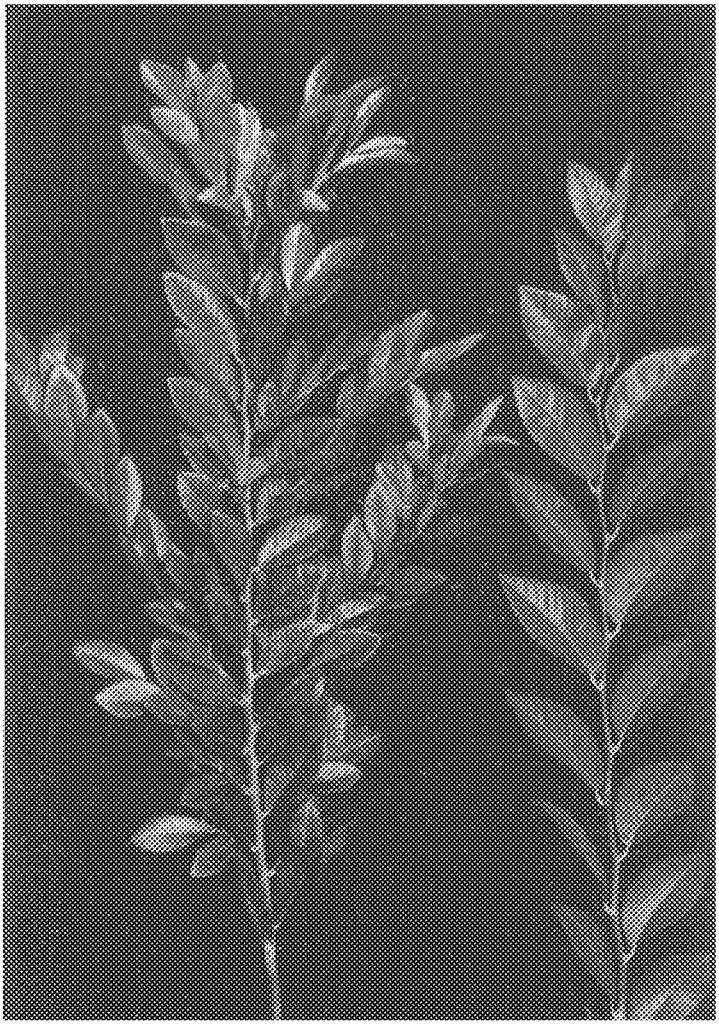

* * * * *